United States Patent [19]

Lehto

[11] Patent Number: 5,160,843
[45] Date of Patent: Nov. 3, 1992

[54] APPARATUS AND METHOD FOR MEASURING GAS CONCENTRATIONS

[75] Inventor: Ari Lehto, Helsinki, Finland

[73] Assignee: Vaisala Oy, Helsinki, Finland

[21] Appl. No.: 731,971

[22] Filed: Jul. 18, 1991

[30] Foreign Application Priority Data

Aug. 3, 1990 [FI] Finland .................................. 903858

[51] Int. Cl.⁵ .......................... H01S 3/22; G01N 21/35
[52] U.S. Cl. ................................ 250/343; 250/338.5; 250/345; 250/493.1
[58] Field of Search .................. 250/493.1, 338.5, 345, 250/343; 313/336, 495

[56] References Cited

U.S. PATENT DOCUMENTS

| | | |
|---|---|---|
| 3,725,701 | 4/1973 | Link . |
| 3,971,968 | 7/1976 | Bachmann et al. ............. 313/629 X |
| 4,274,063 | 6/1981 | Javan ................................... 372/55 |
| 4,721,885 | 1/1988 | Brodie ............................ 313/336 X |
| 4,755,675 | 7/1988 | Rosenfeld et al. .................. 250/343 |
| 4,780,613 | 10/1988 | Bernstein et al. ................... 250/343 |
| 4,967,089 | 10/1990 | Reilly et al. ...................... 250/493.1 |

FOREIGN PATENT DOCUMENTS 0231639  8/1987  European Pat. Off. .

*Primary Examiner*—Constantine Hannaher
*Assistant Examiner*—Edward J. Glink

[57] ABSTRACT

An apparatus and method measures the concentration of a gas. The apparatus comprises a radiation source (70) for emitting radiation onto the gas (79) to be measured, whereby the radiation source (70) is comprised of an anode (4) and a cathode (9), and as an emitting fill gas the same as the gas (79) to be measured; and a radiation detector (74) with which the radiation transmitted through the gas (79) to be measured can be detected. The cathode (9) functions as an electron emitter, and between the anode (4) and the cathode is connected such a low operating voltage that does not cause ionization or essential dissociation of the emitting gas. The design provides an approximate temperature tracking of the radiation source with the ambient temperature.

20 Claims, 2 Drawing Sheets

APPARATUS AND METHOD FOR MEASURING GAS CONCENTRATIONS

FIELD OF THE INVENTION

The present invention relates to an apparatus for measuring gas concentrations.

The invention also concerns a method of measuring gas concentrations.

The invention is intended for use particularly in the concentration measurements of gases or liquids with the help of optical absorption.

DESCRIPTION OF THE BACKGROUND ART

Implementations based on conventional techniques use small solid-state LED and laser components of sufficiently high power output in the visible and near-IR wavelength range. Also used are wide-band emitting halogen-cycle incandescent lamps and so-called "globar" sources.

The solid-state LED and laser components are extremely useful sources of radiation in absorption measurements by virtue of their small size and low power consumption. Their disadvantage is that their output wavelength does not necessarily coincide with the absorption wavelength band of the gas or liquid to be measured. Furthermore, the longest wavelength available from them rarely exceeds 1.5 $\mu$m. Incandescent lamps and globar sources are radiation sources characterized by large size and high power consumption, and their emission spectrum closest approximates the wide-spectrum radiation of a blackbody. The desired wavelengths from such a spectrum must generally be selected by means of filters, which make the construction mechanically complicated, particularly when the filters must be movable for modulation purposes.

U.S. Pat. No. 3,725,701 shows a gas analyzer in which the gas to be analyzed is placed in a container and illuminated with IR radiation emitted by a blackbody. The fluorescence radiation produced in the gas is then employed for the detection of the gas. A disadvantage of this implementation is that it needs a hot blackbody of high energy consumption for use as the emitter of the primary radiation employed for exiting the gas under study. The gas under study behaves like a narrow-band filter, which separates the desired wavelengths from the blackbody radiation. Consequently, the radiation intensity from the gas under study cannot possibly be higher than that of the exciting radiation from the blackbody at the narrow wavelength band in question. Therefore, the available intensity from the gas under study necessarily remains very low, down to a fraction of the total intensity of the exciting radiation emitted by the blackbody.

The EP patent application 231 639 discloses a light source implementation in which a gas is excited with the help of an electric discharge. A disadvantage of such an implementation is that the gas contained in the light source is ionized in the electric discharge. Ionization in turn, however, implies that there is a high gas temperature and Doppler broadening of the spectral lines on one hand, and, on the other hand, that the gas is in a reactive state and undergoes a gradual change in its composition due to chemical reactions. Therefore, the lifespan of light source is limited to a few thousand hours, even if the light source is provided with a gas reservoir, which in turn makes the light source bulky.

SUMMARY OF THE INVENTION

It is an object of the present invention to circumvent the disadvantages of the above-described technology and to achieve an entirely novel apparatus and method for measuring gas concentrations.

The invention is based on the idea of designing the radiation source to contain identical molecules with those of the material under study, whereby the light emitted by the radiation source contains exactly the correct wavelengths. The emitting gas is not ionized and its dissociation is kept minimal. According to the invention, the vibration and rotation energy states of the emitting gas are excited at an appropriate pressure with the help of electron bombardment.

More specifically, the apparatus according to the invention is characterized by a radiation source having an anode, a cathode and the same gas as the gas to be measured and characterized by a radiation detector. The cathode operates as an electron emitter. Between the anode and the cathode, a low operating voltage is connected at which ionization or dissociation of the emitting gas will not occur.

Furthermore, the method according to the invention is characterized by the steps of emitting radiation onto a gas to be measured, detecting this radiation and the emitted radiation being generated by nonionizingly exciting the same gas as that to be measured by use of low voltage accelerated emission of electrons.

The invention provides outstanding benefits.

Because the electron emitter of the radiation source according to the present invention operates at an extremely low thermal power level, typically in the order of 150 mW, combined with a shallow height of the gas-filled cavity and operation without ionization, temperature of the gas and simultaneously the entire small-size radiation source stay very close to the ambient temperature. This results in narrow spectral bandwidths of the emitted light by virtue of the concomitantly smaller Doppler shift with respect to that occurring in hot gas as is the case with tubular gas-filled electric-discharge sources. Maintaining a low gas temperature in the measurements is advantageous for absorption measurement techniques, because the gas to be measured itself is generally at a temperature very close to ambient temperature, and consequently, has a narrow absorption linewidth. On the other hand, if the radiation source is subjected to heating in conjunction with, e.g., flue gas measurements, the broadening of emitted linewidths due to the elevated temperature is not particularly deleterious to the accuracy of measurements, because the linewidth of the gas under study also undergoes a similar increase. The small size of the measurement apparatus allows an easy installation in locations actually enclosed by the gas under study.

The silicon/glass construction of the radiation source is characterized in that it can be designed as a part of an integrated optical structure in which the optical waveguides are made of silicon. Then, the useable wavelength range starts from approx. 1 $\mu$m and extends to longer wavelengths in accordance with the IR transmission properties of silicon. The wavelength range extending from approx. 1 $\mu$m to 12 $\mu$m, so important for practical purposes, can be covered using a structure in accordance with the present invention. Wavelengths shorter than 1 $\mu$m are generated with the help of the alternative embodiments of the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention is next examined in detail by way of the exemplifying embodiments illustrated in the attached drawings which are given by way of illustration only, and thus are not limitative of the present invention.

DETAILED DESCRIPTION OF THE PREFERRED EMBODIMENTS

Figure 1:
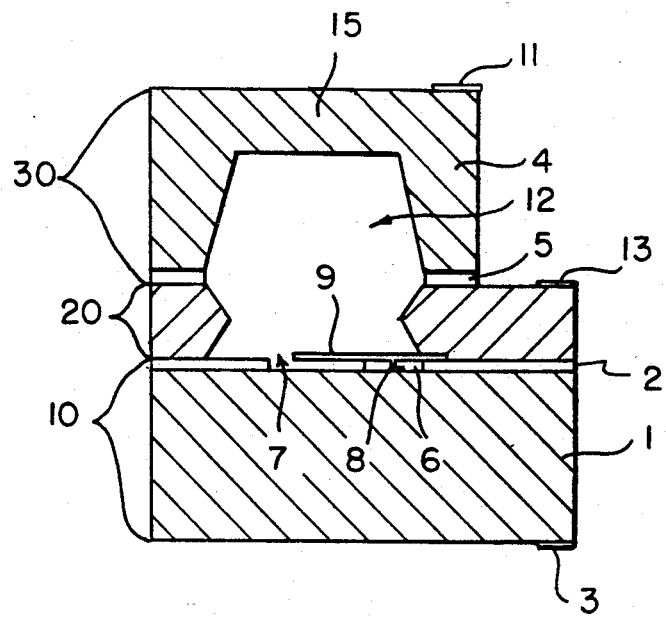
FIG. 1 is a sectional side view of a radiation source according to the invention.
Figure 2:
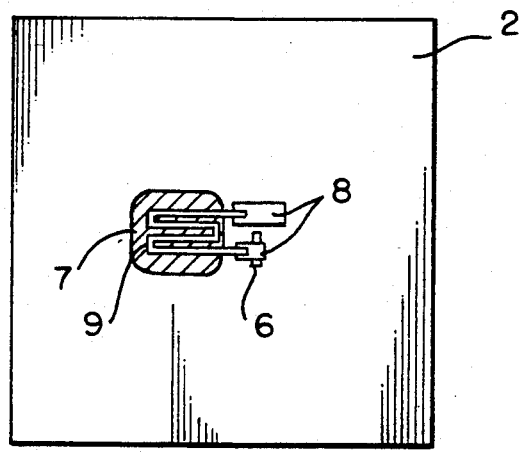
FIG. 2 is a top view of the body part of the radiation source illustrated in FIG. 1.

The radiation source can be made of monocrystalline silicon and glass using conventional micromechanical processing methods of silicon. These include electrostatic bonding of glass on silicon, anisotropic etching of silicon and thin-film metallizing processes. The silicon grade appropriate for use according to the invention is, e.g., p-type (100)-oriented silicon wafer with a thickness of 0.4–1.3 mm. Production is carried out at the wafer level. A body part 10 is comprised of a silicon layer 1 and a glass wafer 2. An intermediate part 20 is of silicon and a cover part 30 is comprised of a cover part silicon layer 4 and a glass wafer 5. The resistivity of the silicon layer 1 and the intermediate part 20 can typically be in the range 0.01–1 ohm cm. The resistivity of the cover part silicon layer 4 can even be increased above 1 ohm cm in order to reduce radiation absorption in this layer to a low value. To produce the body part 10, the top of the silicon wafer is covered by bonding atop the silicon wafer a glass wafer 2 of Corning 7070 glass which is then thinned to a thickness of 100–200 μm using, e.g., diamond paste abrasive grinding. Next, the surface of the glass wafer 2 is polished after a possible lapping. Then, wells 6 and 7 are etched on the glass layer using, e.g., the BHF etch, whereby a glow filament 9 to act as a cathode remains self-supported at the well 7. Next, auxiliary conductors 8 are made with the help of conventional thin-film metallizing using a mechanical mask. The purpose of the auxiliary conductors is to make an electrical contact on one hand via the opening of the well 6 to the body part 1, and on the other hand, via a compression/diffusion bond to the intermediate part 20. The glow filament 9 can be made of, e.g., tungsten by etching from a thin sheet metal (using the lead frame technique). The glow filament is attached to the auxiliary conductors 8 with the help of, e.g., ultrasonic bonding. Alternatively, the cathode can be fabricated as a field emission cathode, such as the cathode described by I. Brodie and J. Muray in "The physics of microfabrication", Plenum Press, 1983. Openings to the intermediate part 20 are first fabricated by etching through the silicon wafer from one or both sides using conventional micromechanical processing methods of silicon, and then producing a contact metallization 13 using a mechanical mask. The silicon wafer forming a top part 30 is first covered with a bonded glass wafer 5 which is polished in the same manner as the surface of the glass wafer 2. Next, a well is etched in the glass wafer 5 down to the silicon wafer surface. The cavity 12 can be made by etching the silicon cover part 4 anisotropically with, e.g., KOH at the area of the well until the well bottom has a thickness of approx. 100 μm. The bottom of the well then acts as an optical exit window 15 of the radiation source. The next step is to produce the contact metallizing 11. After this, all three wafers 10, 20, 30 are bonded together using, e.g., electrostatic bonding. During this process the bonding apparatus is filled with a desired gas mixture at an appropriate pressure, whereby an appropriate gas mixture at a desired pressure remains enclosed in the chip cavities. Finally the chip packet 10, 20, 30 is sawn into chips. Voltage to the glow filament is applied via contact 13 of the intermediate part 20 and contact 3 of the body part 1. The necessary power input to the glow filament varies in the range 100–200 mW, and advantageously is approx. 150 mW. A low voltage of approx. 0.5–5 V is applied between the glow filament 9 acting as the cathode and the cover part 4 acting as the anode. The necessary voltage level depends, i.e., on the fill gas used. The voltage applied between the anode 4 and the cathode 9 determines the intensity of the excitation process, so according to the invention it is essential to maintain as low a voltage level as possible in order to avoid ionization of the gas to be excited. The size of the radiation source chip can appropriately be, e.g., $3 \times 3 \times 4$ mm$^3$, and the chip can be packaged in a TO-5 can, for instance, using such a die-bonding technology in which the body part 1 becomes electrically bonded to said metallic package. An opening of suitable size for transmission of radiation is fabricated at the top of the package.

Figure 3:
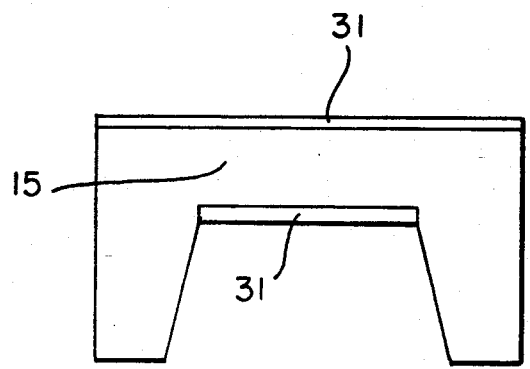
FIG. 3 is a sectional side view of an alternative embodiment of the radiation source according to the invention provided with antireflection coatings.

Silicon has an index of refraction of approx. 3.5 in the near-IR range, so a strong reflection occurs from silicon interfaces at approx. 30% of the radiation incident on the interface. This reflection can be drastically reduced by applying antireflection coatings 31 shown in FIG. 3 to both interface sides of the exit window 15.

Figure 4:
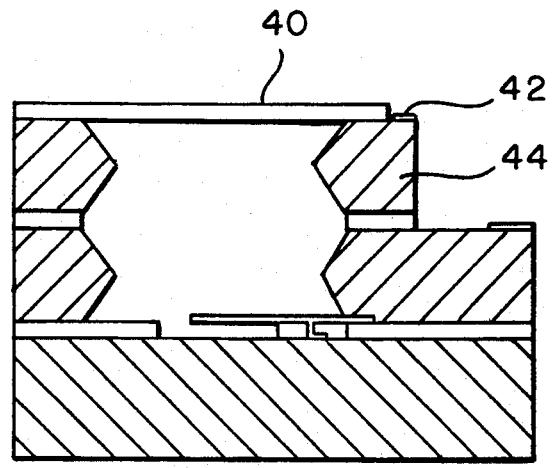
FIG. 4 is a sectional view of a radiation source according to the invention intended for use in the visible and near-IR wavelengths.

In some cases the desired wavelength may fall within the visible wavelength range, which is not transmitted through the silicon window. Then, a structure shown in FIG. 4 can be used having the silicon window replaced by a glass window 40. The glass window 40 is typically capable of light transmission in the range 0.3–3 μm. The electrical contacts are made with the help of metallized areas 42 applied on the conductive silicon areas 44 of the top part.

Figure 5:
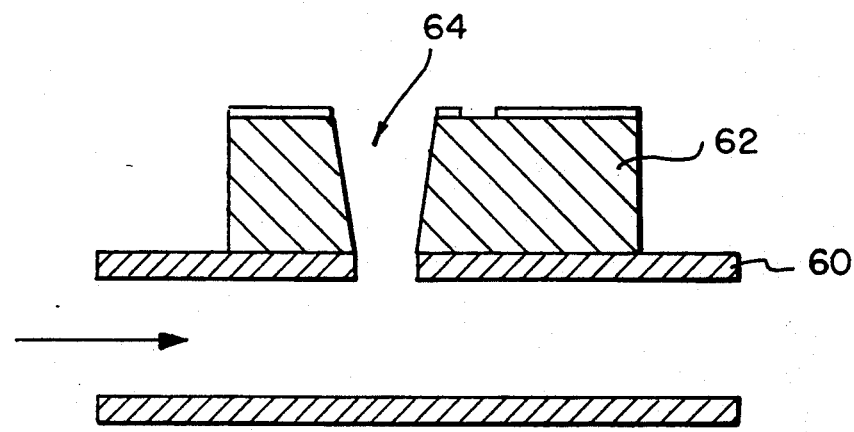
FIG. 5 is a sectional view of a radiation source according to the invention intended for use in conjunction with a continuous gas flow.

The radiation source can also be used in a system requiring gas flow. Then, the radiation source is mounted according to FIG. 5 to a flow pipe 60, whose pressure is maintained at a level appropriate for the advantageous function of the radiation source. In this embodiment the body part 62 is provided with a feed-through hole 64. Intermediate and cover parts such as those illustrated in FIG. 1, for instance, are arranged above the body part 62. The wavelengths and intensities of spectral lines of the emitted radiation are determined by the composition and concentrations of the gas, mixture flowing in the pipe, so the embodiment illustrated in the drawing makes it possible to simultaneously analyze and monitor the gas content in a gas pipe.

Figure 6:
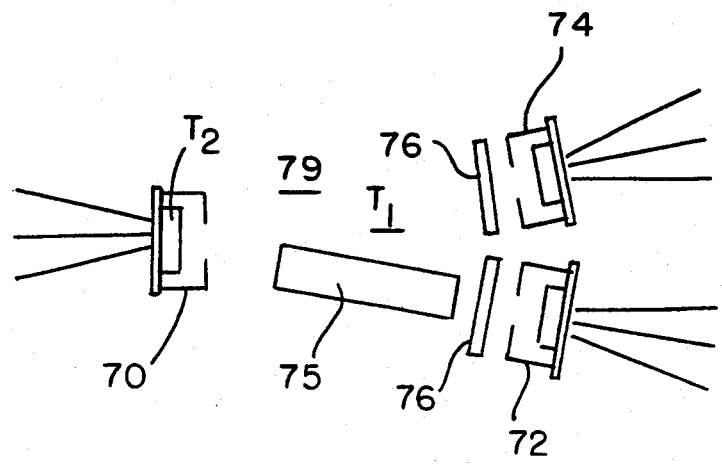
FIG. 6 is a sectional view of a measurement system according to the invention provided with a reference channel.

In the preferred embodiment of the invention, the radiation source is used in a dual-channel absorption analyzer as shown in FIG. 6. The intensity of the radiation source 70 is modulated by varying its anode voltage at a frequency of, e.g., 1 kHz, whereby the long-term drift effects of the system can be eliminated. In practice the modulation is implemented as pulsed amplitude modulation so that the anode voltage is taken to ground potential for one half-cycle and to the normal operating voltage (0.5–5 V) for the other half-cycle. Thus, no polarity reversal between the anode and cathode occurs. The purpose of the reference channel 75 is to eliminate changes in the radiation source 70 by comparing the signal from the measurement signal against the signal from a reference channel 75. The reference channel 75 does not contain the gas 79 to be measured. Filters 76 placed in front of the measurement channel sensor 74 and the reference channel sensor make 72 it possible to select a desired spectral line of the radiation source if desired. The temperature $T_1$ of the gas 79 to be measured is approximately equal to the temperature of the radiation source 70, and therefore, the temperature $T_2$ of the fill gas.

The gas fill of the radiation source according to the invention can also be a gas mixture, whereby the selection of available spectral lines and operating efficiency of the source will be improved.

The radiation source can be made of silicon and glass, thus offering different wavelengths from near-UV to mid-IR ranges according to the structures used.

Instead of vibrational and rotational states of the gas molecules, it is also possible to utilize the normal excited states of the gas atoms, whereby correspondingly shorter wavelengths of the emitted light are attained.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An apparatus for measuring the concentration of a gas, said apparatus comprising:
    a radiation source for emitting radiation on the gas to be measured, said radiation source further being comprised of
      an anode and a cathode, the cathode operates as an electron emitter, and
      an emitting fill gas the same as the gas to be measured, and
    a radiation detector capable of detecting the radiation transmitted through said gas to be measured, and between said anode and said cathode is connected such a low operating voltage at which minimal ionization or dissociation of the emitting fill gas occurs.

2. The apparatus as defined in claim 1, wherein said cathode is a glow filament.

3. The apparatus as defined in claim 1, said cathode is a field emission cathode.

4. The apparatus as defined in any foregoing claim, wherein an operating voltage of less than 5 V is connected between said anode and said cathode.

5. The apparatus as defined in claim 1, wherein the radiation source is used as a dual-channel absorption analyzer, the apparatus further comprises filters, a reference channel sensor and reference channel means for eliminating changes in radiation source, both the radiation detector and the reference channel sensor having one of the filters, and the reference channel means failing to contain the gas to be measured.

6. The apparatus as defined in claim 1, wherein said radiation source is fabricated as a layered silicon structure into which the emitting fill gas is enclosed during a bonding stage of layers of the silicon structure.

7. The apparatus as defined in claim 6, further comprising an exit window for said radiation source being provided in the silicon structure, the exit window being made of silicon.

8. The apparatus as defined in claim 6, wherein one layer of the silicon structure has an exit window provided therein and further comprising antireflection coatings provided on at least one of an inner side and an outer side of the exit window.

9. The apparatus as defined in claim 6, wherein three layers are provided as the layers of the silicon structure, a first layer being a body part, as second layer being an intermediate part and a third layer being a top part, the intermediate part being located between the body part and the top part.

10. The apparatus as defined in claim 9, further comprising an exit window located in the top part of the silicon structure, the window being made of silicon.

11. The apparatus as defined in claim 9, further comprising an exit window located in the top part of the silicon structure, the window being made of glass and being applied to silicon areas of the top part.

12. The apparatus as defined in claim 9, wherein the body part of the silicon structure has a feed-through hole defined therein and wherein the body part is provided on a flow pipe whereby the apparatus is used in a system requiring gas flow.

13. The apparatus as defined in claim 9, further comprising a first glass wafer provided between the body part and the intermediate part and a second glass wafer provided between the intermediate part and the top part, at least one well being etched in each of the glass wafers.

14. The apparatus as defined in claim 13, wherein the first glass wafer has a first well with the cathode being provided therein and a second well having auxiliary conductors provided therein, the second well being divided into two sections with each section having one auxiliary conductor, one of the auxiliary conductors being electrically connected between the cathode and the body part and another of the auxiliary conductors being electrically connected between the cathode and the intermediate part of the silicon structure.

15. The apparatus as defined in claim 14, wherein the intermediate part and the body part have contacts provided on outer surfaces thereof.

16. A method for measuring concentration of a gas, the method comprising the steps of:
    emitting radiation onto the gas to be measured;
    detecting transmitted radiation;
    generating said emitted radiation by nonionizingly exciting an emitting gas which is the same as the gas to be measured by low-voltage-accelerated emission of electrons such that minimal ionization or dissociation of the emitting gas occurs.

17. The method as defined in claim 16, further comprising the step of exciting vibrational and rotational states of the emitting gas by electrons submitted by a flow filament.

18. The method as defined in claim 16, wherein the emitting gas is excited by an electron emitter operating at a thermal power level of generally 100–200 mW.

19. The method as defined in any of claims 16, 17 or 18, comprising the step of connecting an operating voltage of max. 5 V between an anode and a cathode provided as a radiation source for emitting radiation on the gas to be measured.

20. The method as defined in claim 18, wherein the thermal power level is generally 150 mW.

* * * * *